United States Patent [19]

Vallet

[11] 4,177,271
[45] Dec. 4, 1979

[54] HYDROXY- AND OXO-SUBSTITUTED α-BENZYLIDENYLCYCLOALKANES

[75] Inventor: Francois M. J. Vallet, Paris, France

[73] Assignee: Unicler, Paris, France

[21] Appl. No.: 927,777

[22] Filed: Jul. 25, 1978

[30] Foreign Application Priority Data

Aug. 4, 1977 [FR] France ................. 77 24062

[51] Int. Cl.$^2$ ............... C07D 317/48; C07D 407/08
[52] U.S. Cl. ............... 424/248.57; 260/340.5 R;
542/429; 542/430; 542/431; 542/433; 542/447;
542/449; 424/252
[58] Field of Search ............... 542/429–431,
542/433, 447, 449; 260/340.5 R; 424/282,
248.57

[56] References Cited

U.S. PATENT DOCUMENTS 3,468,881  9/1969  Szmuszkovicz ............... 542/429

FOREIGN PATENT DOCUMENTS 561942   8/1958  Canada ............... 260/340.5 R
2154536  5/1973  France .
2253503 12/1973  France ............... 424/282

OTHER PUBLICATIONS

Swoboda et al., "Phytochemical Studies", in J.C.S., vol. C #2, 1967, pp. 161, 162.

Primary Examiner—Arthur P. Demers
Attorney, Agent, or Firm—Stevens, Davis, Miller & Mosher

[57] ABSTRACT

Hydroxy- and oxo-substituted α-benzylidenylcycloalkanes having the formula:

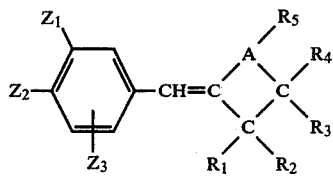

$Z_1$, $Z_2$ and $Z_3$ each denotes a methoxy group or $Z_1$ or $Z_2$ and $Z_3$ together denote a methylenedioxy group, and $Z_3$ is a hydrogen atom or chlorine atom, one of the symbols $R_1$ and $R_2$ denotes a hydrogen atom and the other denotes a hydroxyl group or, together the two denote an oxygen atom; $R_3$ denotes a hydrogen atom or a methyl group; $R_4$ denotes a hydrogen atom, a methyl group or an aminomethyl group, the amino group being a dimethylamino, diethylamino, morpholino, 4-methylpiperazino or piperidino radical; or $R_3$ and $R_4$ together denote a piperonylidene group; $R_5$ denotes a hydrogen atom or a methyl group, and A forms, with the carbon atoms to which it is attached, a cyclopentane, cyclohexane, indane, tetrahydronaphthalene, perhydronaphthalene or piperidine structure and the pharmaceutically acceptable addition salts of the compounds containing an amino group.

The compounds have pharmacological activity on the central nervous system.

4 Claims, No Drawings

HYDROXY- AND OXO-SUBSTITUTED α-BENZYLIDENYLCYCLOALKANES

The objects of the present invention are α-benzylidenecycloalkanones and the corresponding alcohols, their preparation, and their use as medicaments.

The compounds of the invention have the formula

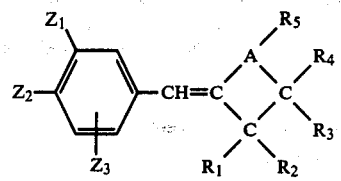

in which
- $Z_1$, $Z_2$ and $Z_3$ each denotes a methoxy group or $Z_1$ and $Z_2$ together denote a methylenedioxy group, and $Z_3$ is a hydrogen atom or chlorine atom,
- one of the symbols $R_1$ and $R_2$ denotes a hydrogen atom and the other denotes a hydroxyl group or, together, the two denote an oxygen atom,
- $R_3$ denotes a hydrogen atom or a methyl group,
- $R_4$ denotes a hydrogen atom, a methyl group or an aminomethyl group, the amino group being a dimethylamino, diethylamino, morpholino, 4-methylpiperazino or piperidino radical; or $R_3$ and $R_4$ together denote a piperonylidene group,
- $R_5$ denotes a hydrogen atom or a methyl group, and
- A forms, with the carbon atoms to which it is attached, a cyclopentane, cyclohexane, indane, tetrahydronaphthalene, perhydronaphthalene or piperidine structure, as well as the pharmaceutically acceptable addition salts of the compounds containing an amino group.

The invention more particularly concerns the compounds of the formula (I) in which A forms together with the carbon atoms to which it is attached a cyclohexane group, that is to say the compounds of the formula

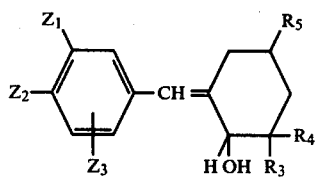

in which the different symbols have the same meaning as in formula (I).

The compounds may be prepared by condensing aldehydes of the formula

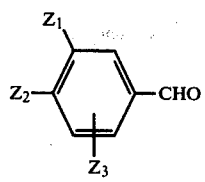

with a ketone of the formula

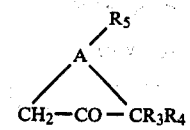

in which formulae the symbols $Z_1$, $Z_2$, $Z_3$, $R_3$, $R_4$, A and $R_5$ have the meanings given above, in an aqueous or alcoholic medium and in equimolecular amounts.

A α-ethylenic ketone of the formula

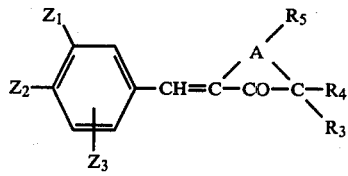

is thus obtained.

In order to obtain the corresponding α-ethylenic alcohol of the formula

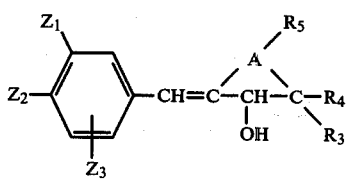

the keytone (Ia) is reduced, for example by means of potassium or sodium borohydride in an alcoholic medium. In these formulae, the symbols $Z_1$, $Z_2$, $Z_3$, $R_3$, $R_4$, A and $R_5$ have the same meanings as in the formula (I).

In order to prepare the compounds of the general formula (I) containing a $R_4$ group=aminomethyl, the following method may advantageously be employed. The ketone of the formula (Ia) in which $R_3=R_4=H$ is prepared, and aminomethylation is carried out to introduce the $R_4$ group by means of the amine corresponding to $R_4$ and formaldehyde.

The following examples illustrate the preparation of the compounds of the invention.

EXAMPLE 1

2-(3,4-methylenedioxybenzylidene)-6-methylcyclohexanone or 2-piperonylidene-6-methylcyclohexanone (Code No. 993)

15 g (0.1 mole) of piperonal, 11.2 g (0.1 mole) of 2-methylcyclohexanone, and 2 sodium hydroxide pellets in 100 cm³ of ethanol are boiled under reflux for 6 hours. The ethanol is distilled off and the product is taken up in water. The product is extracted with chloroform and the oil obtained is distilled (B.P.$_{13\ mm}$=228°). The product is recrystallised from ethanol. M.P.=78°; yield 57%.

EXAMPLE 2

2-(3,4-methylenedioxybenzylidene)-6-methylcyclohexanol or 2-piperonylidene-6-methylcyclohexanol (Code No. 1040).

0.1 mole of the ketone (993) obtained according to Example 1 is dissolved in 300 cm³ of methanol and an aqueous solution of KBH$_4$ is added dropwise. The product obtained is extracted with chloroform and recrystallised from petroleum ether. M.P.=62°; yield 75%.

EXAMPLE 3

2-(piperonylidene)-6-morpholinomethylcyclohexanone and its hydrochloride (Code No. 1325)

23 g of 2-(piperonylidene)-cyclohexanone (0.1 mole), 3 g of paraformaldehyde (0.1 mole) and 12.5 g of morpholine hydrochloride (0.1 mole) in 75 cm³ of absolute ethanol adjusted to a pH-value of 3, are boiled under reflux for 8 hours.

The hydrochloride formed is filtered and recrystallised from nitroethane. M.P.=210°; yield 50%.

A part of the hydrochloride is decomposed with sodium carbonate. The base is recrystallised from ethanol. M.P.=180°.

EXAMPLE 4

2-(piperonylidene)-6-morpholinomethylcyclohexanol (Code No. 1347)

The ketone prepared according to Example 3 is used as starting material and the same technique is employed as in Example 2, except that extraction is carried out with ether and the product is recrystallised from ethanol. M.P.=124°, yield 67%.

The compounds of the preceding examples as well as other compounds prepared in a similar manner are given in the following Table I. The abbreviations used are as follows
  edp=petroleum ether
  DMF=dimethylformamide
  cyclo=cyclohexane.

TABLE I

| Code No. | Formula (ketones) | Code No. of corresponding alcohol | M.P. (°C.) base | M.P. (°C.) hydrochloride (recrystallisation solvent) |
|---|---|---|---|---|
| 993 | | 1040 | 78 (ethanol) | |
| 994 | | 1446 | 120 (ethanol) | |
| 1386 | | 1387 | 100 (ethanol) | |
| 1292 | | 1322 | 180 (acetone) | |
| 1293 | | 1388 | 133 (ethanol) | |
| 1059 | | | 168 (nitromethane) | |

TABLE I-continued

| No. | Structure | No. | mp (solvent) | mp (salt) |
|---|---|---|---|---|
| 1323 | [3,4-ethylenedioxybenzylidene and 3,4-ethylenedioxybenzylidene on N-methyl-piperidin-4-one] | 1324 | 220 (DMF) | |
| 1325 | [3,4-ethylenedioxybenzylidene cyclohexanone with CH₂-morpholine] | 1347 | 180 (ethanol) | 210 (nitroethane) |
| 1348 | [3,4-ethylenedioxybenzylidene cyclohexanone with CH₃ and CH₂-N(CH₃)₂] | 1349 | 52 (edp) | 202 |
| 1350 | [3,4-ethylenedioxybenzylidene cyclohexanone with CH₃ and CH₂-morpholine] | 1351 | 116 (ethanol) | 185 |
| 1352 | [3,4-ethylenedioxybenzylidene cyclohexanone with CH₃ and CH₂N-piperazine-N-CH₃] | 1353 | 132 (ethanol) | 202 (2HCl) |
| 1354 | [3,4-ethylenedioxybenzylidene decalone] | 1355 | 114 (methanol) | |
| 1274 | [2-chloro-4,5-ethylenedioxybenzylidene-6-methylcyclohexanone] | 1275 | 108 (ethanol) | |
| 1266 | [3,4-dimethoxybenzylidene-6-methylcyclohexanone] | 1267 | 67 (cyclohexane) | |

TABLE I-continued

| Code No. | Formula | Code No. of corresponding ketones | M. P. (°C.) base | M. P. (°C.) hydrochloride |
|---|---|---|---|---|
| 1268 | (3,4,5-trimethoxybenzylidene)-2-methylcyclohexanone | 1269 | 95 (ethanol) | |
| 1270 | (2,3,4-trimethoxybenzylidene)-2-methylcyclohexanone | 1271 | 62 (edp) | |

| Code No. | Formula (alcohols) | Code No. of corresponding ketones | M. P. (°C.) base | M. P. (°C.) hydrochloride |
|---|---|---|---|---|
| | | | (recrystallisation solvent) | |
| 1040 | | 993 | 62 (edp) | |
| 1446 | | 994 | oil $n_D^{25} = 1.5675$ | |
| 1387 | | 1386 | 52 (edp 60 cyclo 40) | |
| 1322 | | 1292 | 122 (isopropanol) | |
| 1388 | | 1293 | 146 (ethanol) | |
| 1324 | | 1323 | 180 (ethanol 50 water 50) | |
| 1347 | | 1325 | 194 | 236 (ethanol) |

TABLE I-continued

| No. | Structure | No. | Property | mp (solvent) |
|---|---|---|---|---|
| 1349 | (3,4-ethylenedioxybenzylidene)-cyclohexane with OH, CH₃, CH₂N(CH₃)₂ | 1348 | oil $\eta = 1.5535$ | 185 (ethanol) |
| 1351 | (3,4-ethylenedioxybenzylidene)-cyclohexane with OH, CH₃, CH₂N-morpholine | 1350 | 95 | 252 (ethanol) |
| 1353 | (3,4-ethylenedioxybenzylidene)-cyclohexane with OH, CH₃, CH₂N-(N-methylpiperazine) | 1352 | 128 | 250 (2HCl) (ethanol) |
| 1355 | (2-chloro-4,5-ethylenedioxybenzylidene)-cyclohexane with OH, CH₃ | 1354 | 120 | |
| 1275 | (2-chloro-4,5-ethylenedioxybenzylidene)-cyclohexanone with CH₃ | 1274 | 95 (pentane) | |
| 1267 | (3,4-dimethoxybenzylidene)-cyclohexane with OH, CH₃ | 1266 | oil $n_D^{25} = 1.5460$ | |
| 1269 | (3,4,5-trimethoxybenzylidene)-cyclohexane with OH, CH₃ | 1268 | oil $n_D^{25} = 1.5518$ | |
| 1271 | (2,4-dimethoxybenzylidene)-cyclohexane with OH, CH₃ | 1270 | oil $n_D^{25} = 1.5398$ | |

The compounds of the invention have been tested pharmacologically.

A. Toxicity

The $LD_{50}$ of the products was determined in mice by the intraperitoneal route according to the "Log-Probits" method of Miller and Tainter (Proc. Soc. Exptl. Biol. Med. 1944; 57, 261–264).

B. Activity on the central nervous system

This was investigated by observing the behaviour of the animal by studying the modification in hexobarbital-induced narcosis and antagonism vis-a-vis reserpine.

1. Modification of hexobarbital-induced narcosis

Mice, each weighing about 20 g, received intraperitoneally the product being investigated. Half an hour later sodium hexobarbital was injected by the same route at a dosage of 70 mg/kg.

The animals were placed on a hot plate maintained at a constant temperature of 27° C. Sleep is considered to have occurred as soon as a mouse, placed in the dorsal decubitus position, is incapable of turning over onto its paws.

The narcosis potentialisation is evaluated from the percentage increase in sleep time induced by hexobarbital (T).

2. Antagonism vis-a-vis reserpine (Blepharospasm)

(Chen G., and Bohner B., (1961) J. pharmacol Exptl. Therap. 131, 179).

Reserpine when administered intraperitoneally to mice in a dosage of 5 mg/kg causes the eyelids to close more or less completely in the majority of animals. The administration of certain products will inhibit the blepharospasm produced by reserpine.

Swiss male mice are distributed into groups of 10 mice, and each experiment includes at least 3 groups:
- a control group that receives only the solvent and reserpine
- a group treated with a reference product (we chose Imipramine)
- a treated group that receives the product being tested.

The products under investigation are administered intraperitoneally at 30 minutes or 2 hours before intraperitoneal injection of reserpine in a dosage of 5 mg/kg, so as to study their activity as a function of time.

The degree of ptosis for each eye and each animal is observed every 30 minutes for 4 to 5 hours, using RUBIN's score method. The activity of the product is determined by comparison with the result obtained with the treated control group. The inhibition of blepharospasm is recorded from 0 to +++.

The results obtained in the various tests are given in the following Table II.

TABLE II

| Code No. | $LD_{50}$ (mg/kg) IP | Blepharospasm IP mg/kg | | Narcosis potentialisation mg/kg | T |
|---|---|---|---|---|---|
| 993 | 2000 | 200 | 0 | 200 | 385% |
| 994 | 2000 | 200 | 0 | 200 | 103% |
| 1386 | 1300 | 130 | 0 | 130 | 190% |
| 1292 | $DL_0 \geq 2000$ | 200 | 0 | 200 | 62% |

TABLE II-continued

| Code No. | $LD_{50}$ (mg/kg) IP | Blepharospasm IP mg/kg | | Narcosis potentialisation mg/kg | T |
|---|---|---|---|---|---|
| 1293 | $DL_0 \geq 2000$ | 200 | 0 | 200 | 30% |
| 1059 | $DL_0 \geq 2000$ | 200 | 0 | 200 | 0 |
| 1323 | $DL_0 \geq 2000$ | 200 | 0 | 200 | 66% |
| 1325 | 250 | 25 | ± | 25 | 121% |
| 1348 | 100 | 10 | ± | 10 | 39% |
| 1350 | 750 | 75 | ± | 50 | 139% |
| 1352 | 150 | 15 | 0 | 15 | 0 |
| 1354 | ≥2000 | 200 | + | 200 | 66% |
| 1274 | $DL_0 \geq 2000$ | 200 | ± | 200 | 99% |
| 1266 | 700 | 70 | 0 | 70 | 0 |
| 1268 | 1000 | 100 | ± | 100 | 60% |
| 1270 | 1000 | 100 | ± | 100 | .60% |
| 1040 | 1000 | 100 | ++ | 100 | 174% |
| 1446 | 1500 | 150 | ± | | |
| 1387 | 100 | 10 | 0 | 10 | 40% |
| 1322 | 1500 | 150 | 0 | 150 | 116% |
| 1388 | $DL_0 > 200$ | 200 | 0 | 200 | 10% |
| 1324 | $DL_0 \geq 2000$ | 200 | 0 | 200 | 83% |
| 1347 | 1000 | | | 100 | 60% |
| 1349 | 100 | 10 | ± | 10 | 10% |
| 1351 | 700 | 70 | 0 | 70 | 101% |
| 1353 | 150 | 15 | 0 | 15 | 34% |
| 1355 | 2000 | 200 | 0 | 200 | 49% |
| 1275 | 2000 | 200 | 0 | 200 | 56% |
| 1267 | 900 | 90 | ± | 90 | .46% |
| 1269 | 1100 | 110 | 0 | 110 | 66% |
| 1271 | 500 | 50 | 0 | 50 | 0 |

As can be seen from the results of the pharmacological tests described above, the compounds of the invention act on the central nervous system.

They may be used in particular as adjuncts in anticomitial therapy, and as anxiolytics, anti-depressants, hypnotics and tranquilisers. Compound No. 1040 has been found to be particularly useful as an anti-depressant.

The compounds of the invention may be formulated in conjunction with a pharmaceutically compatible excipient for oral administration, for example in the form of tablets, pills or capsules, for parenteral administration in the form of solutions for injection, or for endorectal administration in the form of suppositories.

The daily dosage will be of the order of 50 to 300 mg orally and, where appropriate, 5 to to 50 mg by injection in the case of the soluble compounds.

What I claim is:
1. 2-piperonylidene-6-morpholinomethylcyclohexanol.
2. 2-piperonylidene-6-methylcyclohexanol.
3. A method for treating anxious or depressive syndromes in a patient which comprises administering to said patient a pharmaceutical compound of claim 1 or 2.
4. A pharmaceutical composition for treatinan axious or depressive syndrome which contains a compound of claim 1 or 2 and a pharmaceutically acceptable carrier therefor.

* * * * *